United States Patent
Nakai et al.

(10) Patent No.: US 10,261,150 B2
(45) Date of Patent: Apr. 16, 2019

(54) MAGNETIC RESONANCE IMAGING APPARATUS AND PROCESSING METHOD

(71) Applicant: HITACHI, LTD., Tokyo (JP)

(72) Inventors: Norimasa Nakai, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 917 days.

(21) Appl. No.: 14/761,155

(22) PCT Filed: Jan. 20, 2014

(86) PCT No.: PCT/JP2014/050945
§ 371 (c)(1),
(2) Date: Jul. 15, 2015

(87) PCT Pub. No.: WO2014/125876
PCT Pub. Date: Aug. 21, 2014

(65) Prior Publication Data
US 2015/0377995 A1    Dec. 31, 2015

(30) Foreign Application Priority Data

Feb. 12, 2013    (JP) ................................ 2013-024992

(51) Int. Cl.
*G01R 33/48* (2006.01)
*A61B 5/055* (2006.01)
(Continued)

(52) U.S. Cl.
CPC .......... *G01R 33/4828* (2013.01); *A61B 5/055* (2013.01); *A61B 5/4872* (2013.01);
(Continued)

(58) Field of Classification Search
CPC ............ G01R 33/5676; G01R 33/5673; G01R 33/567; G01R 33/5659; G01R 33/56581;
(Continued)

(56) References Cited

U.S. PATENT DOCUMENTS 8,698,495 B2 *   4/2014  Nehrke ................ G01R 33/246
                                                      324/309
2004/0010191 A1  1/2004  Yatsui
2014/0194728 A1* 7/2014  Vahala ..................... A61N 7/02
                                                      600/411

FOREIGN PATENT DOCUMENTS

JP      6-98875         12/1994
JP      2001-340314     12/2001
WO      WO02/13693      2/2002

OTHER PUBLICATIONS

International Search Report in PCT/JP2014/050945.

* cited by examiner

*Primary Examiner* — Tung X Nguyen
(74) *Attorney, Agent, or Firm* — Cooper & Dunham LLP

(57) ABSTRACT

A magnetic resonance imaging apparatus that can display an image showing conditions of tissues such as water and fat more accurately is provided. For this purpose, the signal processing unit 110 processes signals of each pixel of the first image 506 generated based on an NMR signal for each pixel of the first image 506 in order to generate the second image 509 and determines an order of processing unprocessed pixels of the first image 506 by preferentially selecting the unprocessed pixels with a high signal strength from among a plurality of unprocessed pixels for which no process has not been performed yet that are adjacent to the already-processed pixels of the first image 506.

15 Claims, 14 Drawing Sheets

(51) Int. Cl.
*A61B 5/00* (2006.01)
*G01R 33/565* (2006.01)
*G01R 33/56* (2006.01)

(52) U.S. Cl.
CPC ........ *A61B 5/742* (2013.01); *G01R 33/56563* (2013.01); *A61B 5/4869* (2013.01); *G01R 33/5608* (2013.01)

(58) Field of Classification Search
CPC ........ G01R 33/56572; G01R 33/56563; G01R 33/56554; G01R 33/56545; G01R 33/56536; G01R 33/56527; G01R 33/56518; G01R 33/56509; G01R 33/565; G01R 33/56391; G01R 33/56383; G01R 33/56375; G01R 33/56366; G01R 33/56358; G01R 33/5635; G01R 33/56341; G01R 33/56333; G01R 33/56325; G01R 33/56316; G01R 33/56308; G01R 33/563; G01R 33/5619; G01R 33/5618; G01R 33/5617; G01R 33/5616; G01R 33/5615; G01R 33/5614
See application file for complete search history.

MAGNETIC RESONANCE IMAGING APPARATUS AND PROCESSING METHOD

TECHNICAL FIELD

The present invention relates to a magnetic resonance imaging apparatus, in particular, a processing technique for a tissue contrast image in a magnetic resonance imaging apparatus.

BACKGROUND ART

A Magnetic Resonance Imaging (hereinafter, MRI) apparatus measures a Nuclear Magnetic Resonance (hereinafter, NMR) signal generated by atomic nuclear spin comprising an object, in particular human body tissue and images shapes and tissue of the head, abdomen, extremities, etc. two-dimensionally or three-dimensionally.

In case of obtaining an image using an MRI apparatus, an image with various tissue contrasts can be obtained by changing parameters such as an Echo Time (hereinafter, described as TE) and a Repetition Time (hereinafter, described as TR) or performing image computation. A method to obtain an image separating water and fat for image accuracy improvement is referred to as the Dixon method.

Additionally, there are the 2-point Dixon method and the 3-point Dixon method with static magnetic field correction in which a function to correct influence of static magnetic field inhomogeneity is added to the Dixon method. When a phase rotation amount due to the static magnetic field inhomogeneity is calculated using these methods, arithmetic processing referred to as a phase unwrapping process is performed to prevent water and fat from exchanging. The phase unwrapping process fixes discontinuities caused because a phase beyond the range of $-\pi$ to $\pi$ (this state is referred to as "rotating around a principal value") is expressed within the range of $-\pi$ to $\pi$ again and makes a spatial phase change continuous to express with a value of the phase beyond the range of $-\pi$ to $\pi$.

When rotating around a principal value, two main causes were found in examination by the inventors of the present invention: a case where phase differences between the adjacent pixels is large due to large static magnetic field inhomogeneity and a case where a Signal Noise Ratio (hereinafter, SNR) is low.

The above unwrapping processing is performed for two-dimensional or three-dimensional data, and the regional expansion method is used. The regional expansion method determines a pixel to start processing first (hereinafter, described as a staring pixel) and expands the processing from the starting pixel to the adjacent pixels spatially, and a pixel value that has already been processed is utilized in processing the adjacent pixels.

In the patent literature 1, a method to reduce principal value rotation by processing from a pixel with a smaller phase difference in order from among the adjacent pixels has been suggested. Specifically, a phase difference inclination image is generated, and a pixel with a smaller phase difference is processed first.

CITATION LIST

Patent Literature

PTL 1: U.S. Pat. No. 7,227,359

SUMMARY OF INVENTION

Technical Problem

In the PTL 1, a method in which a phase difference inclination image is generated to reduce principal value rotation by processing from a pixel with a smaller phase difference in order has been suggested. However, because an SNR is not considered at all, reduction cannot be performed for principal value rotation caused by noise due to a low SNR, which eventually results in a problem that accuracy of an image showing comprised tissue is lowered.

The purpose of the present invention is to provide a magnetic resonance imaging apparatus that can display an image showing a tissue state more accurately or to provide the processing method.

Solution to Problem

A magnetic resonance imaging apparatus related to the invention to solve the above problem is characterized by comprising a magnetic field generating unit generating a static magnetic field and a gradient magnetic field to an object; a high-frequency pulse irradiating unit irradiating a high-frequency pulse; a reception unit receiving an NMR signal from the object; a display unit displaying a generated diagnostic image; and a signal processing unit generating a first image based on the NMR signal, determining an order of performing a phase unwrapping process for each pixel forming the first image from among a plurality of pixels for which the phase unwrapping process has not been performed yet and that are adjacent to pixels for which the phase unwrapping process has already been performed within the pixels of the first image by selecting unprocessed pixels with a high signal strength preferentially, and generating a second image by performing a phase unwrapping process for the unprocessed pixels in the determined order.

Advantageous Effects of Invention

According to the present invention, a magnetic resonance imaging apparatus that can display an image showing a tissue state more accurately can be obtained.

DESCRIPTION OF EMBODIMENTS

Hereinafter, an embodiment related to the present invention will be described using diagrams. Additionally, the same symbols are used for members having the same functions in all the diagrams for explaining embodiments to apply the invention, and the repeated explanations are omitted.

In the embodiment to be described below, an order to process pixels, i.e. an unwrapping process path can be determined properly, and this can avoid rotating around a principal value. Specifically, pixels can be processed in order from a pixel with a large SNR or from an adjacent pixel with a small phase difference and a large SNR, which can avoid rotating around a principal value. For example, in the PTL 1, an SNR is not considered at all, which generates a state where rotating around a principal value cannot be avoided. In a state where rotating around a principal value cannot be avoided, for example, a process to exchange water and fat is performed, and a case where an image in which water and fat were exchanged is displayed is caused.

Also, pixels can be processed in a relatively short time in an embodiment to be described below. On the contrary to this, in the PTL 1 for example, because a phase difference gradient image is generated to process adjacent pixels, processing time is lengthened. Hereinafter, an embodiment of the present invention will be described.

Figure 1:
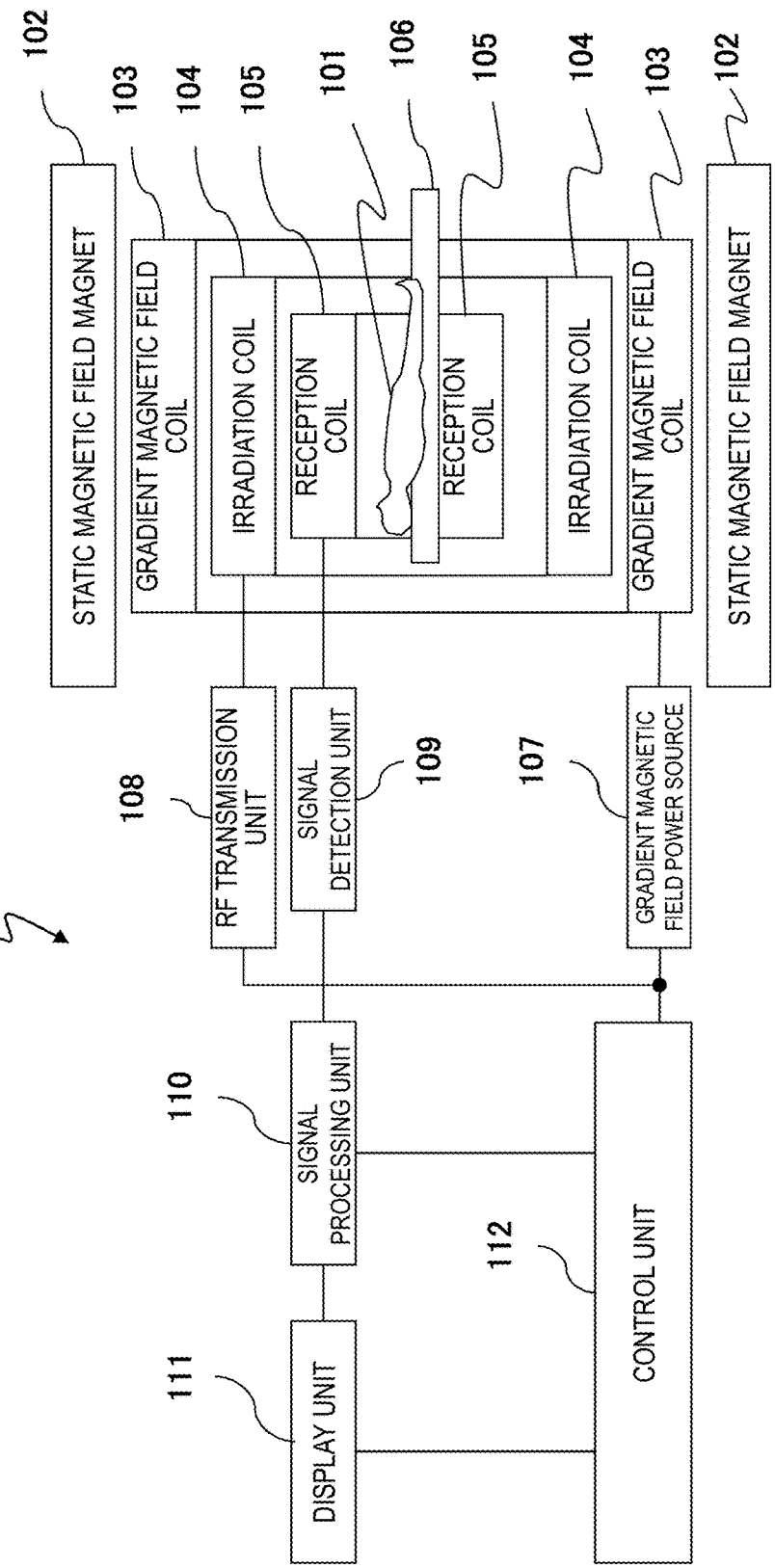
FIG. 1 is a configuration diagram of a magnetic resonance imaging apparatus that is an embodiment of the present invention.

FIG. 1 is a schematic diagram of the overall configuration of the MRI apparatus 1 that is an embodiment of the invention. The MRI apparatus 1 has the static magnetic field magnet 102 generating a static magnetic field, the gradient magnetic field coil 103 generating a gradient magnetic field, the irradiation coil 104 irradiating a high-frequency magnetic field pulse (hereinafter, described as an RF pulse) to the object 101, and the reception coil 105 detecting an NMR signal from the object 101 in the surroundings of the object 101 and further has the bed 106 placing the object 101.

The static magnetic field magnet 102 is disposed in a space of a certain extent to place the object 101, is comprised of a permanent magnet, superconducting magnet, or a normal conducting magnet, and generates a homogeneous static magnetic field in a direction parallel or vertical to the body axis of the object 101.

The gradient magnetic field coil 103 applies gradient magnetic fields in the three axis directions X, Y, and Z to the object 101 based on a signal from the gradient magnetic field power source 107. According to how the gradient magnetic fields are applied, an imaging cross section of the object 101 is set.

The irradiation coil 104 generates an RF pulse according to a signal from the RF transmission unit 108. Atomic nuclei of atoms comprising a biological tissue in an imaging cross section of the object 101 that is set by the gradient magnetic field coil 103 is excited by the RF pulse, an NMR phenomenon is induced.

An echo signal being an NMR signal is generated by the NMR phenomenon of atomic nuclei of atoms comprising a biological tissue of the object 101 induced by the RF pulse from the irradiation coil 104, and the echo signal is detected in the signal detection unit 109 through the reception coil 105 disposed near the object 101. The detected echo signal is signal-processed in the signal processing unit 110 to convert into an image. The converted image is displayed in the display unit 111.

The control unit 112 controls the gradient magnetic field power source 107 and the RF transmission unit 108 so as to repeatedly generate an RF pulse and the respective gradient magnetic fields of a slice encode, a phase encode, and a frequency encode in a certain predetermined pulse sequence, and then further controls the signal processing unit 110.

In a static magnetic field to be generated by the static magnetic field magnet 102 of the above MRI apparatus 1 in a space placing the object 101, spatial inhomogeneity in the static magnetic field itself caused by the magnetic structure and spatial inhomogeneity in the static magnetic field caused by that magnetic sensitivity differs depending on each part of the object 101 placed on the static magnetic field space are generated (hereinafter, these are referred to together as "static magnetic field inhomogeneity"). As described above, there are the 2-point Dixon method and the 3-point Dixon method with static magnetic field correction in which a function to correct influence of static magnetic field inhomogeneity is added to the Dixon method. The 3-point Dixon method performs imaging three times while changing TE, and the 2-point Dixon method performs imaging twice while changing TE. Because the 3-point Dixon method performs imaging three times while changing TE, it takes more time than the 2-point Dixon method, but a more accurate image can be obtained. Although a case of using the 2-point Dixon method is described in embodiments of the present invention, the 3-point Dixon method can also be applied similarly and effective.

Figure 2:
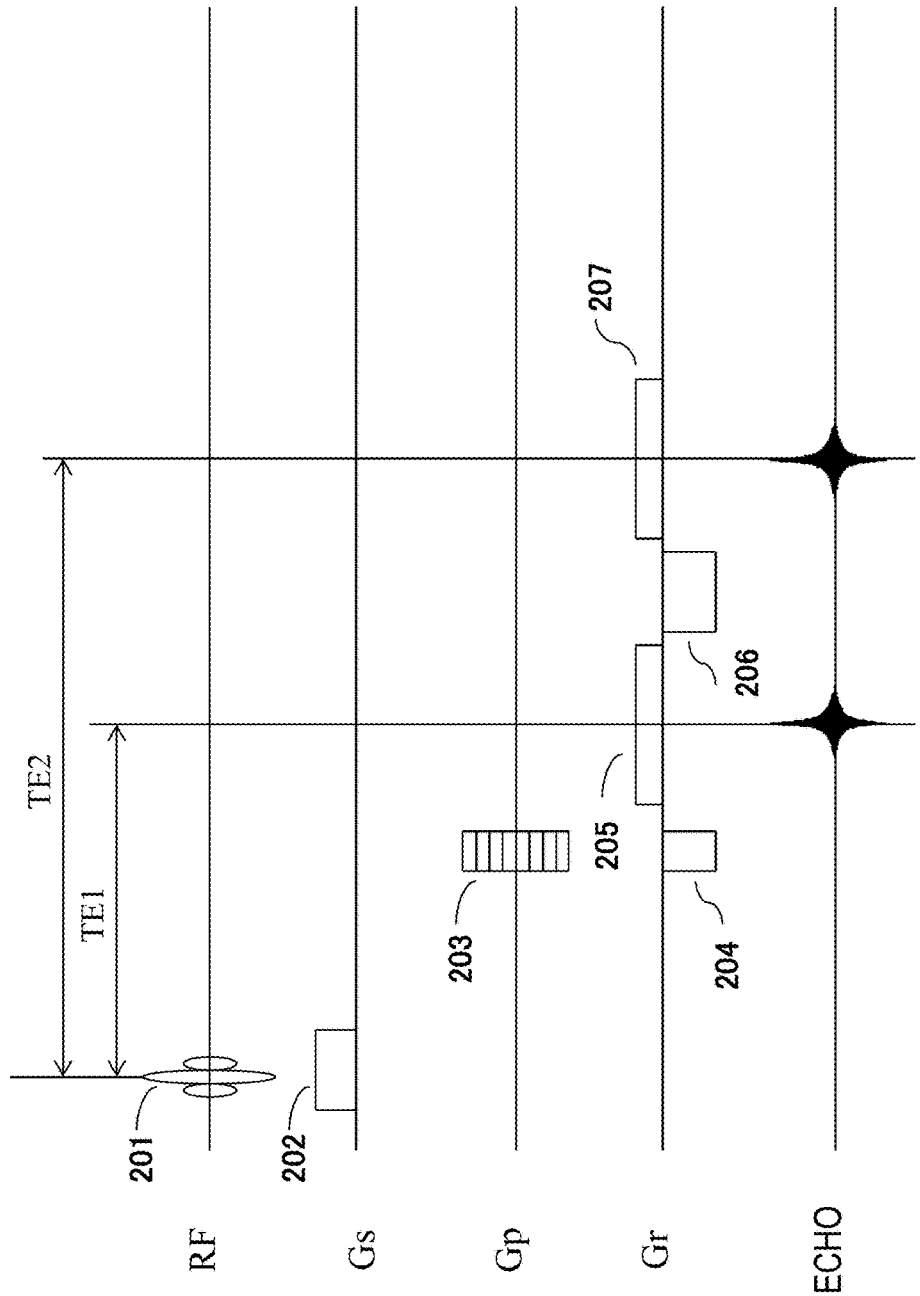
FIG. 2 is an explanatory diagram showing a gradient echo sequence of the 2-point Dixon method.

FIG. 2 is an example of a pulse sequence to be used for the 2-point Dixon method to be used in embodiments of the present invention. This pulse sequence is a Gradient Echo sequence that obtains two types of image data with a different TE. The control unit 112 performs the following control and transmits this pulse sequence via the RF transmission unit 108. That is, the control unit 112 controls so as to excite only a target cross section by irradiating the RF pulse 201 and applying the slice encoding gradient magnetic field 202 at the same time.

Then, the phase encoding gradient magnetic field 203 for encoding positional information is applied by the gradient magnetic field coil 103, the negative-direction frequency encoding gradient magnetic field (diphase pulse) 204 is applied, and then the positive-direction frequency encoding gradient magnetic field 205 to generate a first echo signal from the RF pulse 201 after TE1 elapses. Next, the second negative-direction frequency encoding gradient magnetic field (rewind pulse) 206 and the positive-direction frequency encoding gradient magnetic field 207 are applied to generate a second echo signal from the RF pulse 201 after TE2 elapses. In case of obtaining an image in which water and fat are separated, for example, TE1 is a time when echo signals obtained from water and fat become opposite phases each other, and TE2 is a time when echo signals obtained from water and fat become the same phase each other.

Then, such a sequence is repeatedly performed by the number of times of phase encoding while changing a area of the phase encoding gradient magnetic field 203, echo signals by the number of phase encoding obtains k-space data in the signal detection unit 109 via the reception coil 105, and then the k-space data is processed in the signal processing unit 110. In the signal processing unit 110, the two-dimensional Fourier transform is performed for the k-space data to obtain two types of image data with a different TE. These images are displayed in the display unit 111. In the 2-point Dixon method, the two types of pulses: TE in which water and fat phases become the same and TE in which water and fat phases become opposite are set to obtain an image where water and fat are separated.

The pulse sequence method shown in FIG. 2 is an example, and there are various pulse sequences of a gradient echo to be used in the 2-point Dixon method. The pulse sequence method shown in FIG. 13 is an example of another method, and the pulse sequence method shown in FIG. 14 is an example of the other method.

Figure 13:
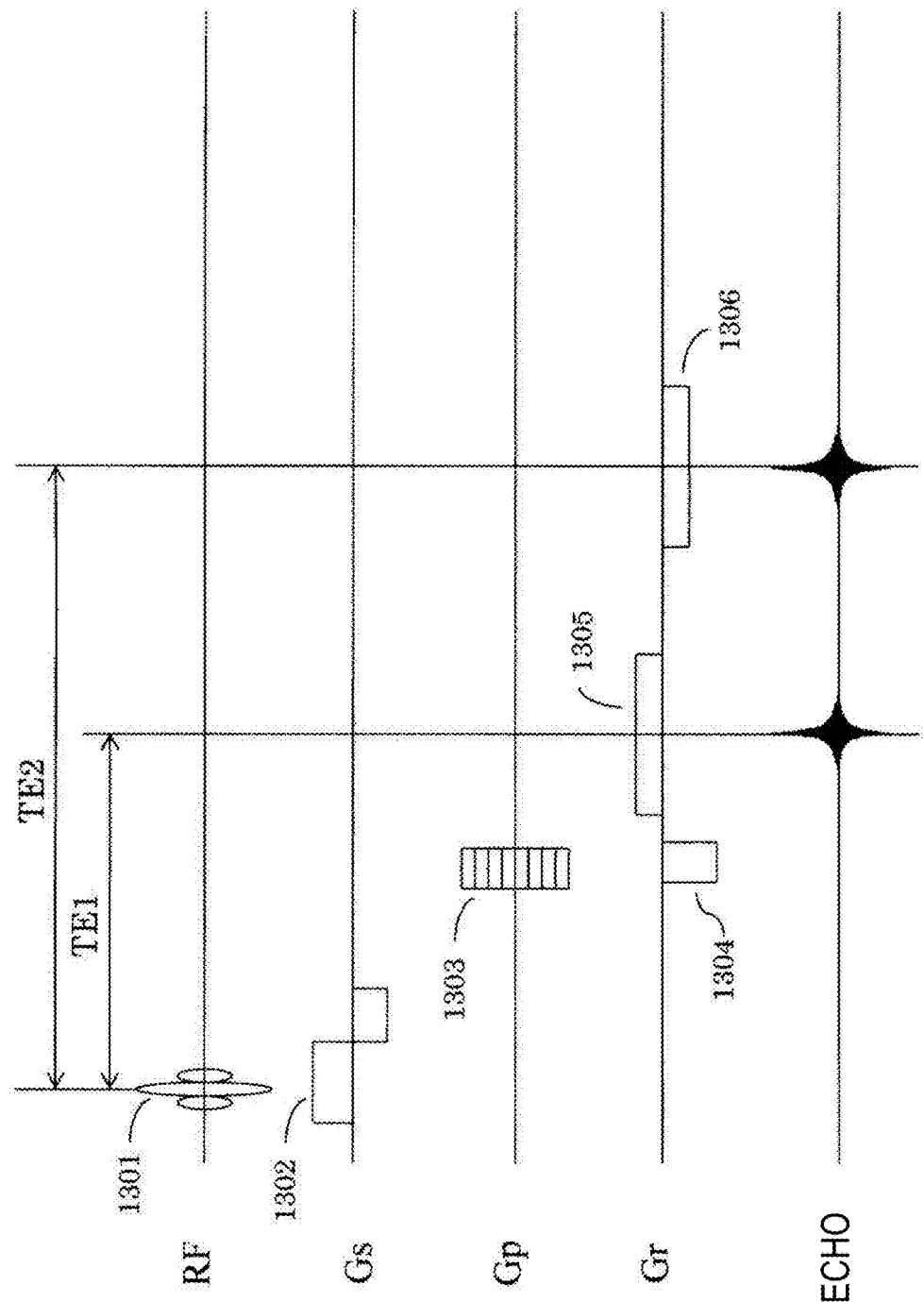
FIG. 13 is an explanatory diagram showing the other method than the gradient echo sequence of the 2-point Dixon method shown in FIG. 2.

The method shown in FIG. 13 is a method to generate a second echo signal in a negative-direction frequency encoding gradient magnetic field after TE2 elapses. Compared to FIG. 2, there is an advantage that a time between TE1 and TE2 can be shortened. The control unit 112 controls so as to excite only a target cross section by irradiating the RF pulse 1301 and applying the slice encoding gradient magnetic field 1302 at the same time. The phase encoding gradient magnetic field 1303 for encoding positional information is applied, the negative-direction frequency encoding gradient magnetic field (diphase pulse) 1304 is applied, and then the positive-direction frequency encoding gradient magnetic field 1305 is applied to generate a first echo signal from the RF pulse 1301 after TE1 elapses. Next, the negative-direction frequency encoding gradient magnetic field 1306 is applied to generate a second echo signal from the RF pulse 1301 after TE2 elapses. Here, the RF pulse 1301, the slice encoding gradient magnetic field 1302, the phase encoding gradient magnetic field 1303, the frequency encoding gradient magnetic field 1304, and the frequency encoding gradient magnetic field 1305 correspond respectively to the RF pulse 201, the slice encoding gradient magnetic field 202, the phase encoding gradient magnetic field 203, the diphase pulse 204, and the frequency encoding gradient magnetic field 205 of FIG. 2, and the functions and the effects are the same basically.

Figure 14:
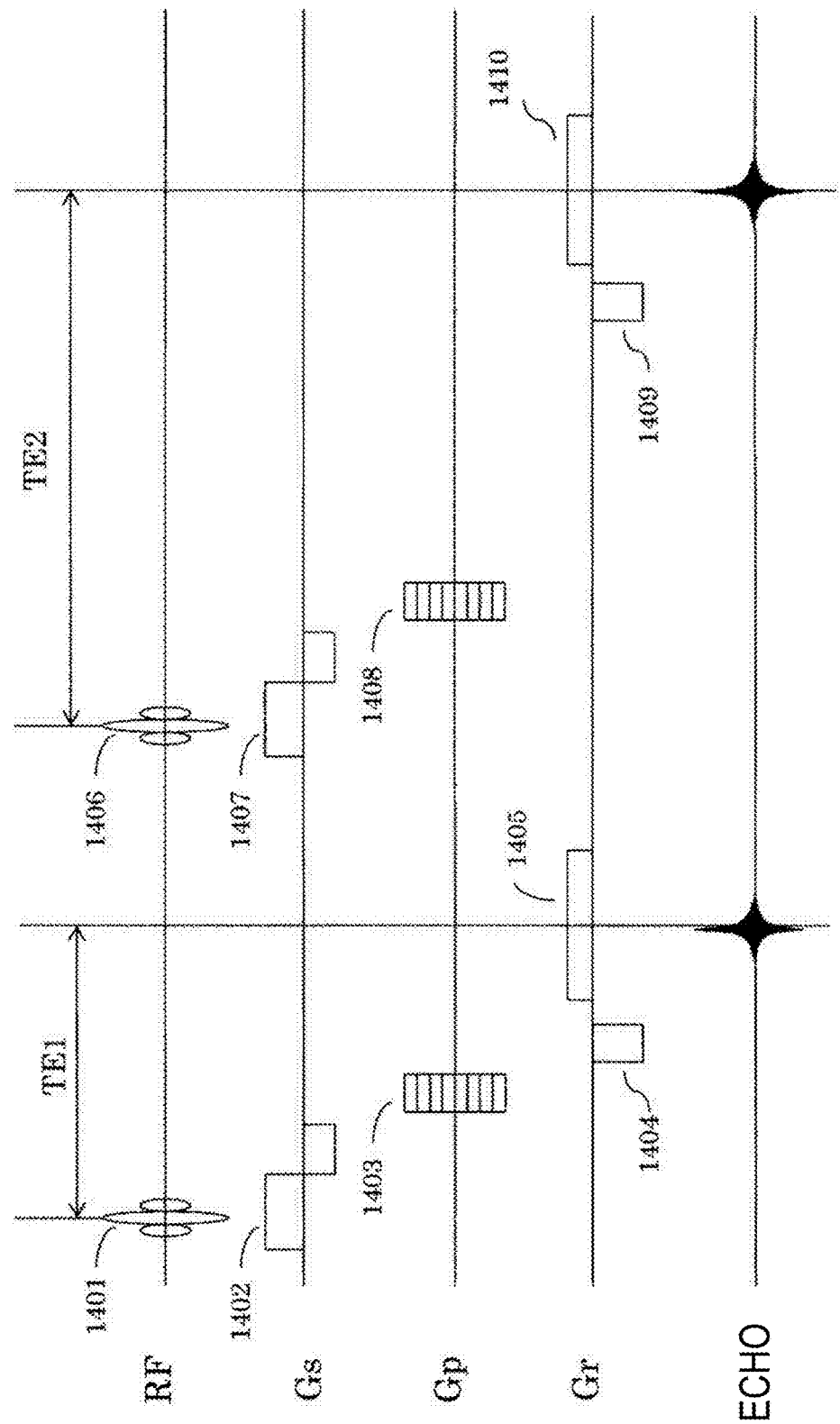
FIG. 14 is an explanatory diagram showing the other method than the gradient echo sequence of the 2-point Dixon method shown in FIG. 13.

FIG. 14 shows a method to generate a first echo after TE1 elapses and a second echo after TE2 elapses using different RF pulses. The control unit 112 controls so as to excite only a target cross section by irradiating the RF pulse 1401 and applying the slice encoding gradient magnetic field 1402 at the same time. The phase encoding gradient magnetic field 1403 for encoding positional information is applied, the negative-direction frequency encoding gradient magnetic field (diphase pulse) 1404 is applied, and then the positive-direction frequency encoding gradient magnetic field 1405 is applied to generate a first echo signal from the RF pulse 1401 after TE1 elapses. Similarly, it is controlled again so as to excite only a target cross section by irradiating the RF pulse 1406 and applying the slice encoding gradient magnetic field 1407 at the same time. The phase encoding gradient magnetic field 1408 for encoding positional information is applied, the negative-direction frequency encoding gradient magnetic field (diphase pulse) 1409 is applied, and then the positive-direction frequency encoding gradient magnetic field 1410 is applied to generate a second echo signal from the RF pulse 1406 after TE2 elapses.

As described above, the method shown in FIG. 2 is a method to generate an echo signal based on the RF pulse 201 after TE1 elapses and to additionally generate an echo signal based on the same RF pulse 201 after TE2 elapses. On the contrary to this method, the method shown in FIG. 14 is a method to generate an echo signal based on the RF pulse 1401 after TE1 elapses and to generate an echo signal to be generated after TE2 elapses based on the RF 1406. Although there is such a difference, the basic functions and effects of the RF pulses 1401 and 1406 are the same as the RF pulse 201 of FIG. 2. Also, the basic functions and effects of the slice encoding gradient magnetic fields 1402 and 1407 are the same as the slice encoding gradient magnetic field 202. The basic functions and effects of the phase encoding gradient magnetic fields 1403 and 1408 are the same as the phase encoding gradient magnetic field 203 of FIG. 2. The basic functions and effects of the negative-direction frequency encoding gradient magnetic field (diphase pulse) 1404 and the positive-direction frequency encoding gradient magnetic field 1405 or the negative-direction frequency encoding gradient magnetic field (diphase pulse) 1409 and the positive-direction frequency encoding gradient magnetic field 1410 are the same as the diphase pulse 204 and the frequency encoding gradient magnetic field 205 of FIG. 2.

Figure 3:
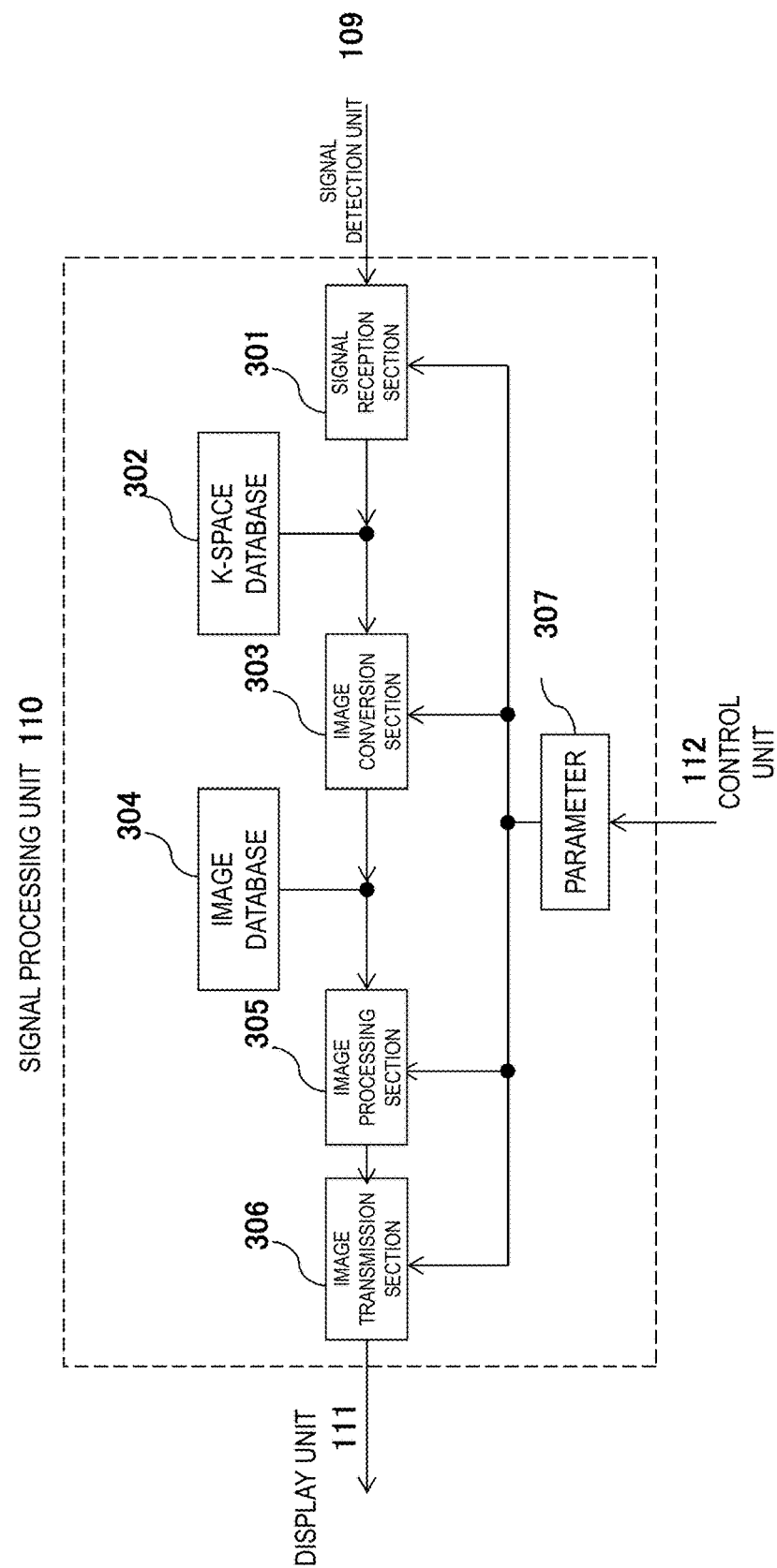
FIG. 3 is a configuration diagram showing processing functions of a signal processing unit.

Next, the configuration of the signal processing unit 110 to execute the 2-point Dixon method specifically will be described. FIG. 3 is a functional block diagram for explaining the processing function of the signal processing unit 110.

The signal reception section 301 stores an echo signal from the signal detection unit 109 in the k-space database 302 based on information about arranging in k-space comprised of a slice encode, a phase encode, and a frequency encode of the parameter 307. The image conversion section 303 performs the Fourier transform for k-space data stored in the k-space database 302 to convert into an image, and then stores it in the image database 304. The image processing section 305 performs image processing for the image stored in the image database 304 and passes it over to the image transmission section 306. The image processing includes, for example, a process to generate water and fat images and a process to correct uneven sensitivity of the reception coil 105. The image transmission section 306 transmits an image-processed image to the display unit 111.

The parameter 307 includes information about a slice encode, a frequency encode, and a phase encode in a pulse sequence required by the signal reception section 301 as well as parameters and control information such as an image matrix and filtering required by the image conversion section 303, the image processing section 305, and the image transmission section 306 and obtains them from the control unit 112.

Figure 4:
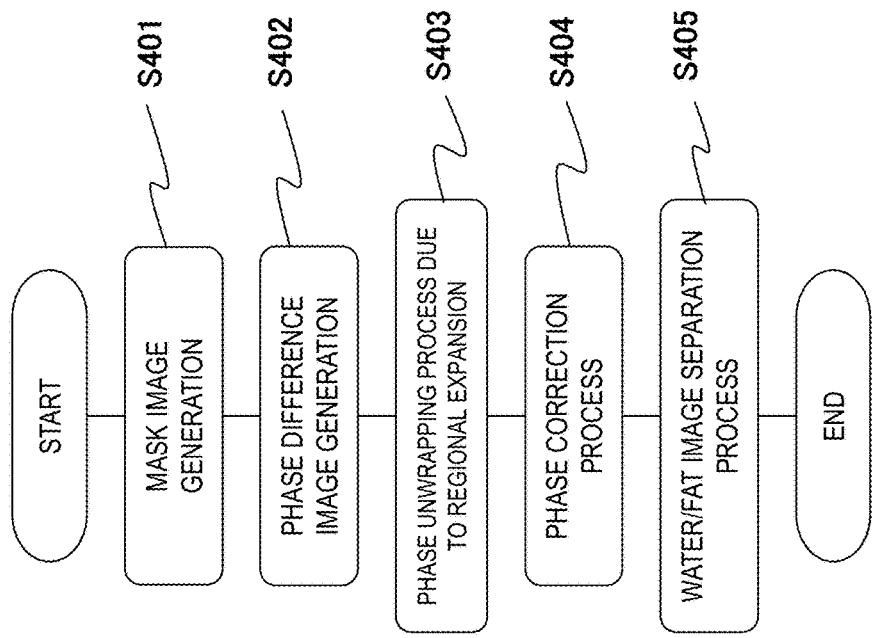
FIG. 4 is a process flow diagram of the 2-point Dixon method.
Figure 5:
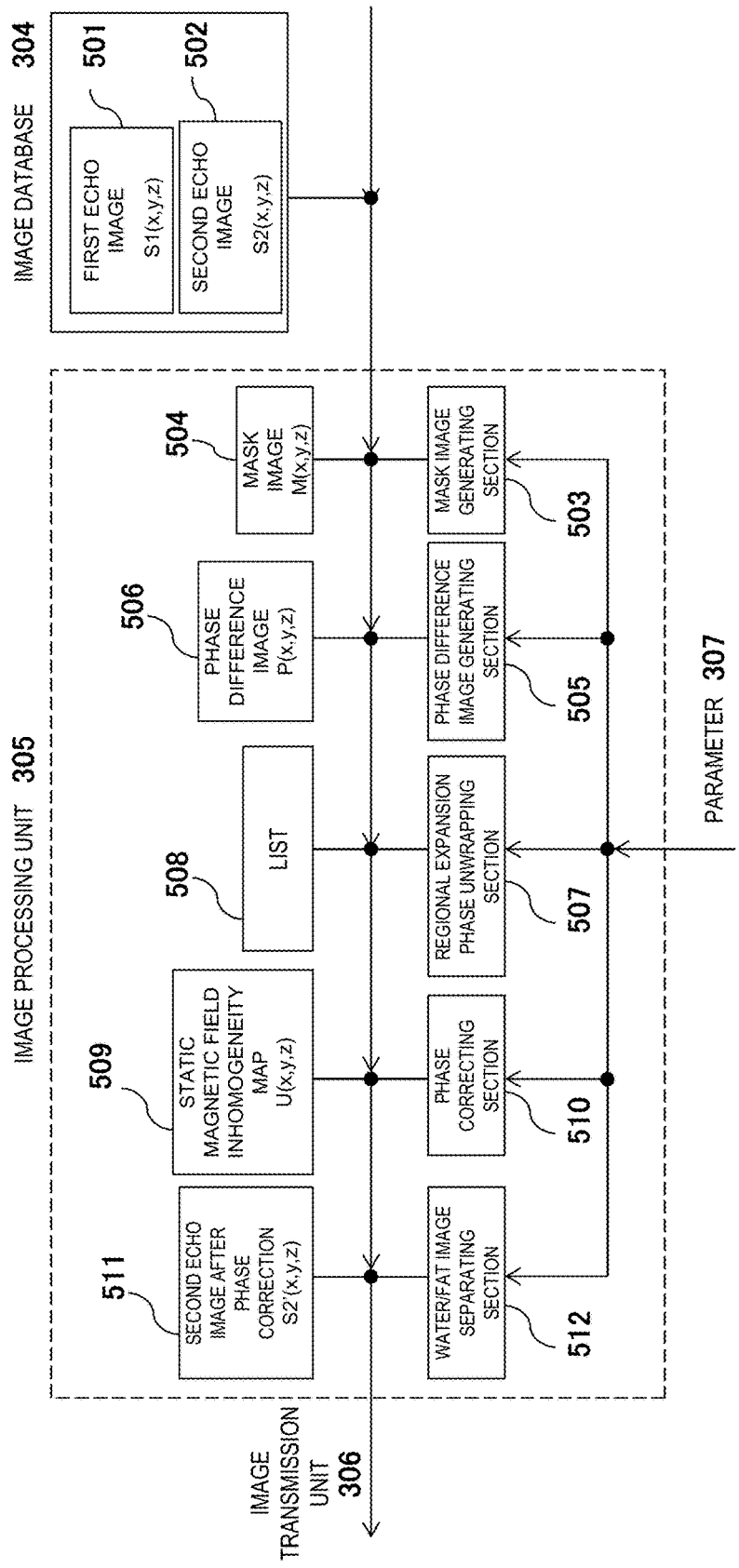
FIG. 5 is a configuration diagram showing processing functions of an image processing section by the 2-point Dixon method.

Next, an MRI apparatus of an embodiment of the present invention and a processing procedure for a phase correction algorithm will be described based on FIGS. 4 and 5. FIG. 4 is a processing flow diagram explaining the present embodiment. A program for executing the present processing is stored in the image processing section 305, and the image processing section 305 executes processing in each step explaining based on FIG. 4. FIG. 5 is a functional configuration diagram explaining processing functions of the image processing section 305 executing a process flow of the present embodiment. Additionally, the present embodiment describes a phase unwrapping process due to regional expansion in the 2-point Dixon method.

An image of complex data obtained by setting to TE in which water and fat phases become opposite is specified as the first echo image 501, and an image of complex data obtained by setting to TE in which water and fat phases become the same is specified as the second echo image 502.

Operations in an embodiment of the present invention will be described based on the flow chart shown in FIG. 4.

(Step S401)

The mask image generating section 503 generates the mask image 504 showing a region to perform a phase unwrapping process from the first echo image 501 and the second echo image 502 stored in the image database 304. The mask image 504 is generated to exclude a noise-only region having no object apparently from the region for the phase unwrapping process. For example, there are the following three methods to generate a mask image.

[Mask Image Generation Method 1]

The method 1 generates a mask image by performing a binarization process for the first echo image 501.

$$\begin{cases} M(x, y, z) = 1 & (|S1(x, y, z)| \geq \text{Threshold}) \\ M(x, y, z) = 0 & (|S1(x, y, z)| < \text{Threshold}) \end{cases} \quad \text{[Formula 1]}$$

"S1(x, y, z)" is the first echo image 501, and "M(x, y, z)" is the mask image 504. "x", "y", and "z" show an abscissa, an ordinate, a slice number of an image respectively. "Threshold" is a threshold value separating a region having an object from a region having no object. Because the first echo image 501 is an image in which water and fat phases become opposite, a low SNR region where water and fat cancel out each other can be excluded from a region for phase unwrapping. A method to calculate a threshold value will be described later.

[Mask Image Generation Method 2]

The method 2 generates a mask image by performing a binarization process for the second echo image 502.

$$\begin{cases} M(x, y, z) = 1 & (|S2(x, y, z)| \geq \text{Threshold}) \\ M(x, y, z) = 0 & (|S2(x, y, z)| < \text{Threshold}) \end{cases} \quad \text{[Formula 2]}$$

"S2(x, y, z)" is the second echo image 502. Because the second echo image 502 is an image in which water and fat phases become the same, water and fat do not cancel out each other, a region having an object can be accurately extracted. A method to calculate a threshold value will be described later.

[Mask Image Generation Method 3]

The method 3 further identifies a region using a ratio of the first echo image 501 and the second echo image 502. Because the first echo image 501 is an image in which water and fat phases become opposite and the second echo image 502 is an image in which water and fat phases become the same, a region where there are water and fat can be excluded exactly by dividing the first echo image 501 by the second echo image 502 to perform threshold value processing. Because a phase error easily occurs in a region where there are water and fat, excluding a region where there are water and fat from regional expansion is effective as a method to reduce principal value rotation of phase unwrapping.

$$\begin{cases} M(x, y, z) = 1 & (|S1(x, y, z)/S2(x, y, z)| \geq \text{Threshold2}) \\ M(x, y, z) = 0 & (|S1(x, y, z)/S2(x, y, z)| < \text{Threshold2}) \end{cases} \quad \text{[Formula 3]}$$

A Mask image of [Formula 3] is used in combination with a mask image generated with [Formula 1] or [Formula 2] and becomes a final mask image by taking a logical product of [Formula 1] and [Formula 3] or [Formula 2] and [Formula 3]. An appropriate value is set for the threshold value "Threshold2" within the range of 0 to 1 in light of a mixing ratio of water and fat. The specific method will be described later. Although [Method 3] is used as a method to generate a mask image in an embodiment of the present invention, the methods 1 and 2 may be used. Next, a method to calculate a threshold value will be described. For example, there are the following two methods to calculate a threshold value.

[Threshold Value Calculation Method]

The method 1 determines a threshold value as one-tenth of the maximum pixel value of the first echo image 501. The method 2 determines a threshold value from a calculated noise level (for example, a three-fold noise level). Utilizing that a ratio of noise components is high in high-frequency components of an image, a high pass filter is provided for the first echo image 501 or the second echo image 502 to generate an absolute value image, which can set an average value of the absolute value image as a noise level. Calculating a noise level more accurately can be achieved by calculating a mode from accumulative density distribution after utilizing that an absolute value image of noise becomes Rayleigh distribution to generate a histogram of the absolute value image. Even in a case where there are high signal components other than noise on the above absolute value image, influence on a noise level can be reduced by generating the histogram to calculate a mode. Although the method 2 is used as a method to calculate a threshold in an embodiment of the present invention, the method 1 may be used.

(Step S402)

The phase difference image generating section 505 generates the phase difference image 506 from the above first echo image 501 and the second echo image 502. First, a phase of the first echo image 501 is subtracted from the second echo image 502.

$$T(x, y, z) = S2(x, y, z) \times \frac{S1^*(x, y, z)}{|S1(x, y, z)|} \quad \text{[Formula 4]}$$

Next, a phase of an image for which the phase subtraction was performed is doubled to generate the phase difference image P (x, y, z) 506. This is performed to align water and fat phases by doubling because the water and fat phases are shifted by 180 degrees from each other.

$$P(x, y, z) = T(x, y, z) \times \frac{T(x, y, z)}{|T(x, y, z)|} \quad \text{[Formula 5]}$$

A signal strength of the phase difference image 506 calculated from [Formula 4] and [Formula 5] becomes a signal strength of the second echo image 502 in which water and fat phases are the same. A signal strength of a phase difference image is used for phase unwrapping of regional expansion to be described later. Therefore, in the regional expansion, phase unwrapping can be performed while avoiding a low SNR region of an image in which water and fat phases are the same. There are two methods for the other signal strengths of the phase difference image 506. The method 1 is a case where a signal strength of the phase difference image 506 is set as a signal strength of the first echo image 501 in which water and fat phases are opposite, and the following [Formula 6] can be used instead of [Formula 4].

$$T(x, y, z) = \frac{S2(x, y, z)}{|S2(x, y, z)|} \times S1^*(x, y, z) \quad \text{[Formula 6]}$$

The method 1 performs phase unwrapping while avoiding a low SNR region where water and fat cancel out each other. The method 2 is a case where both of the first echo image 501 and the second echo image 502 are considered as a signal strength of the phase difference image 506, [Formula 7] or [Formula 8] can be used instead of [Formula 4].

$$T(x, y, z) = S2(x, y, z) \times S1^*(x, y, z) \quad \text{[Formula 7]}$$

$$T(x, y, z) = \frac{S2(x, y, z) \times S1^*(x, y, z)}{\sqrt{|S2(x, y, z)| \times |S1(x, y, z)|}} \quad \text{[Formula 8]}$$

Because the method 2 calculates a product of the first echo image 501 and the second echo image 502, both signal strengths are considered, which can perform a phase unwrapping process more accurately while avoiding a low SNR region of a phase difference image. Although the phase difference image 506 is generated using the method 2 in the present embodiment, any of the above methods may be used.

Also, the phase difference image 506 reduces noise influence by providing a low pass filter or smoothing last, and this can reduce principal value rotation of phase unwrapping.

(Step S403)

The region expansion phase unwrapping unit 507 uses the list 508 to perform a phase unwrapping process for the phase difference image 506 due to regional expansion and generates the static magnetic field inhomogeneity map U (x, y, z) 509. The list 508 is used for a regional expansion process while repeatedly storing and taking out coordinates for regional expansion, phases for which phase unwrapping was performed, and weightings showing an order of the regional expansion for each pixel. The details of the phase unwrapping process due to regional expansion 403 will be described later.

(Step S404)

The phase correcting section 510 performs phase correction for the second echo image S2 (x, y, z) 502 using the static magnetic field inhomogeneity map U(x, y, z) 509. At this time, because no value is included in the pixel where the mask image M(x, y, z) 504 is 0 in the static magnetic field inhomogeneity map U(x, y, z) 509, the value is calculated by extrapolation. Also, because a phase is doubled in the phase difference image generation process in Step 402, a half phase of the static magnetic field inhomogeneity map U(x, y, z) 509 is subtracted from the second echo image S2 (x, y, z) 502 to calculate the phase-corrected second echo image S2' (x, y, z) 511.

$$S2'(x, y, z) = S2(x, y, z) \cdot C^*(x, y, z) \quad \text{[Formula 9]}$$

$$C(x, y, z) = \cos\left(\frac{U(x, y, z)}{2}\right) + i\sin\left(\frac{U(x, y, z)}{2}\right) \quad \text{[Formula 10]}$$

"i" in [Formula 10] shows an imaginary.

(Step S405)

The water/fat image separating section 512 generates a water image and a fat image by respectively complex-adding and complex-subtracting the first echo image 501 and the phase-corrected second echo image 511, and then transmits them to the image transmission section 306.

As described above, the present process flow ends. The program to execute each step in the above process flow is stored in the image processing section 305, and the image processing section 305 executes processes in each step.

Figure 6:
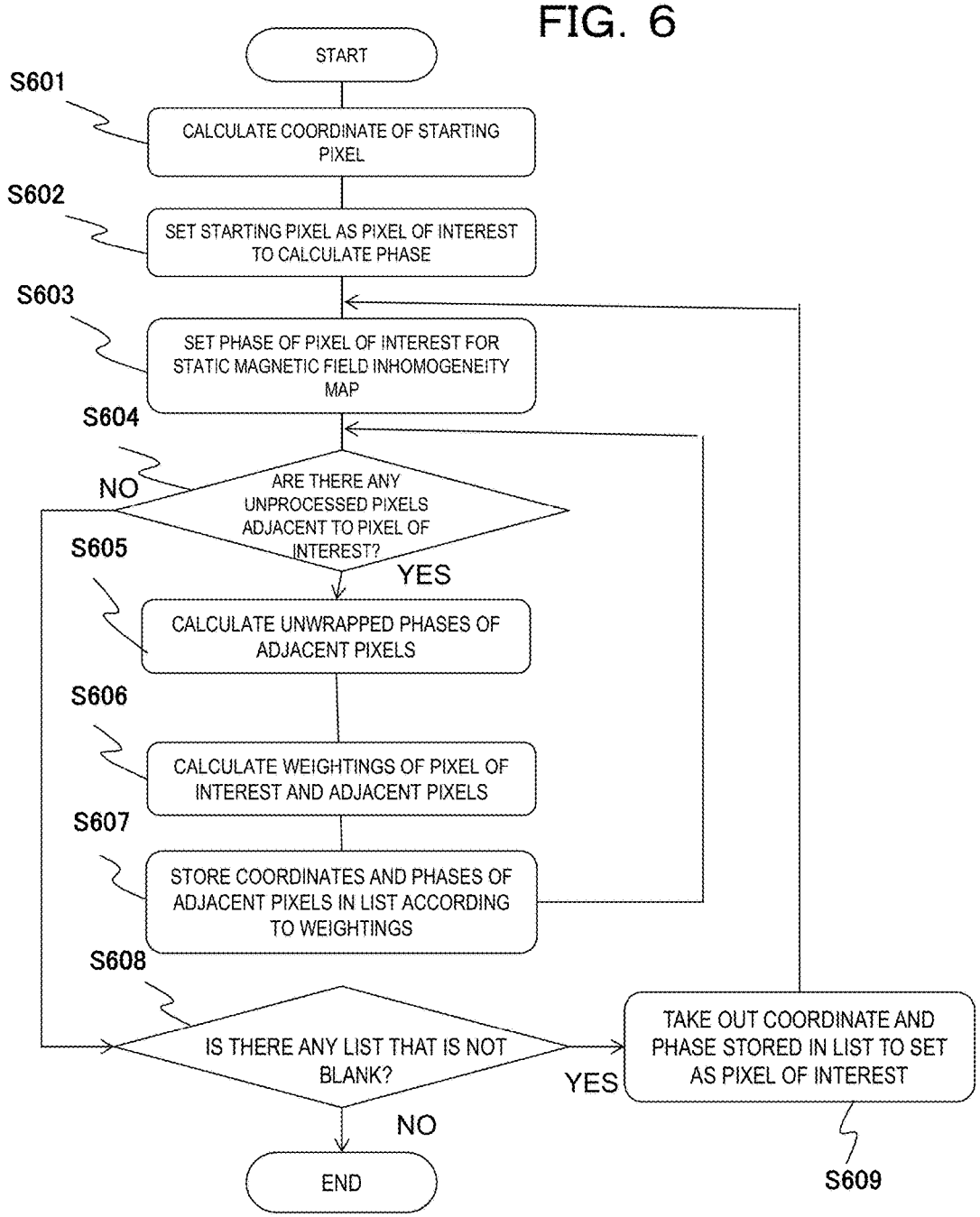
FIG. 6 is an explanatory diagram explaining a phase unwrapping process for regional expansion that is an embodiment.

Next, specific processing contents of Step S403 for the phase unwrapping process by the above regional expansion of the regional expansion phase unwrapping section 507 are shown in FIG. 6, and the phase unwrapping process by the above regional expansion will be described based on the process flow of FIG. 6.

(Step S601)

A coordinate of a pixel to be processed first (hereinafter, described as a starting pixel as described above) is calculated. Several methods to determine a coordinate of the starting pixel are listed below.

1) A method in which a pixel with the maximum signal strength in the first echo image 501 is set as a starting pixel in a region of the mask image M(x, y, z)=1
2) A method in which a pixel with the maximum signal strength in the second echo image 502 is set as a starting pixel in a region of the mask image M(x, y, z)=1
3) A method in which a pixel with the maximum signal strength in the phase difference image 506 is set as a starting pixel in a region of the mask image M(x, y, z)=1

Although the results have no noticeable differences between the above three determination methods, the determination method 1) is used in the present embodiment. However, a starting pixel coordinate may be determined with the methods described in the above 2) and 3).

(Step S602)

A phase is calculated by setting the phase difference image 506 corresponding to a starting pixel coordinate calculated in Step S601 as a pixel of interest. In a case where the starting pixel coordinate is $(x_0, y_0, z_0)$, the phase can be calculated using the following formula.

$$\theta = \arg\{P(x_0, y_0, z_0)\} \quad \text{[Formula 11]}$$

(Step S603)

A phase of a pixel of interest is set for the static magnetic field inhomogeneity map 509. In a case where the pixel of interest coordinate is $(x_0, y_0, z_0)$, the static magnetic field inhomogeneity map 509 is shown in the following formula. By the processing, a phase where an unwrapping process was performed for the pixel of interest is set for a corresponding pixel in the static magnetic field inhomogeneity map 509.

$$U(x_0, y_0, z_0) = \theta \quad \text{[Formula 12]}$$

(Step S604)

Whether pixels adjacent to a pixel of interest (described as adjacent pixels) have unprocessed pixels or not is determined. In a case where the pixel of interest coordinate is $(x_0, y_0, z_0)$, the adjacent pixels are those listed in the following list.

1) A pixel of the mask image M $(x_0-1, y_0, z_0)=1$
2) A pixel of the mask image M $(x_0+1, y_0, z_0)=1$
3) A pixel of the mask image M $(x_0, y_0-1, z_0)=1$
4) A pixel of the mask image M $(x_0, y_0+1, z_0)=1$
5) A pixel of the mask image M $(x_0, y_0, z_0-1)=1$
6) A pixel of the mask image M $(x_0, y_0, z_0+1)=1$ Also, "unprocessed" shows that no value is set for a static magnetic field inhomogeneity map of a coordinate yet and that the processes of Steps 605 and 606 to be described next is not performed as adjacent pixels of this pixel of interest.

(Step S605)

In a case where pixels adjacent to a pixel of interest is unprocessed in Step 604, that is, in case of "Yes" shown in the diagram, an unwrapped phase of the adjacent pixels is calculated. For example, in a case where adjacent pixel coordinates are set as $(x_0-1, y_0, z_0)$, the unwrapped phase $\theta_{unwrap}$ of the adjacent pixels is shown in the following formula.

$$\theta_{unwrap}=U(x_0,y_0,z_0)+\arg\{P(x_0-1,y_0,z_0)\cdot P^{\ddagger}(x_0,y_0,z_0)\} \quad \text{[Formula 13]}$$

The above method calculates a phase difference (range: $-\pi$ to $\pi$) between adjacent pixels and a pixel of interest and adds the calculated phase difference to a phase of the pixel of interest to determine a phase of the adjacent pixels. Although an unwrapped phase is calculated in this method in the present embodiment, the unwrapped phase may be calculated in the other method.

As the other method, the unwrapped phase $\theta_{unwrap}$ of adjacent pixels may be calculated in the following formula.

$$\theta_{unwrap}=\arg\{P(x_0-1,y_0,z_0)\}+2\pi n \quad \text{[Formula 14]}$$

A value in which $\theta_{unwrap}$ is in the range of $U(x_0, y_0, z_0)\pm\pi$ is used for a variable n in [Formula 14].

(Step S606)

Next, a weighting of a pixel of interest and the unprocessed adjacent pixels is calculated. This weighting is a factor to determine a processing order of regional expansion that is a feature of the present embodiment, and there are the four methods as shown below.

[Weighting Method 1]

The first method calculates an inner product of a pixel of interest and the adjacent pixels and performs weighting based on the calculation result, and the following formula can be used in a case where coordinates of the adjacent pixels are $(x_0-1, y_0, z_0)$, for example.

$$W = \text{real}\{P(x_0-1, y_0, z_0)\}\times\text{real}\{P(x_0, y_0, z_0)\} + \text{imaginary}\{P(x_0-1, y_0, z_0)\}\times\text{imaginary}\{P(x_0, y_0, z_0)\} \quad \text{[Formula 15]}$$

"real" of [Formula 15] shows real part data, and "imaginary" shows imaginary part data. As the other calculation method of an inner product, the formulas of [Formula 16] and [Formula 17] can be also used.

$$W=|P(x_0-1,y_0,z_0)|\cdot|P(x_0,y_0,z_0)|\cdot\cos(\psi) \quad \text{[Formula 16]}$$

$$\psi=\arg\{P(x_0-1,y_0,z_0)\cdot P^{\ddagger}(x_0,y_0,z_0)\} \quad \text{[Formula 17]}$$

Since an inner value order is an order of a square of a signal strength, a value in which the inner product is negative is excluded. That is, a value in which the inner product is negative is not stored in the list 508 in the next Step 607. Also, the square root of the inner product may be used. The inner product shows scalar vectors of adjacent pixels, becomes larger as a phase difference is small, and becomes larger as the signal strength is high. Therefore, regional expansion can be performed from a pixel with a large inner product in order while avoiding a region with a large phase difference and a low SNR.

[Weighting Method 2]

The second method excludes a signal strength of a pixel of interest for an inner product.

$$W=|P(x_0-1,y_0,z_0)|\cdot\cos(\psi) \quad \text{[Formula 18]}$$

$$\psi=\arg\{P(x_0-1,y_0,z_0)\cdot P^{\ddagger}(x_0,y_0,z_0)\} \quad \text{[Formula 19]}$$

By considering only a signal strength of adjacent pixels, a processing priority can be determined only with an SNR of the adjacent pixels.

[Weighting Method 3]

The third method sets a difference between a pixel of interest and the adjacent pixel as a weighting.

$$W=|P(x_0,y_0,z_0)-P(x_0-1,y_0,z_0)|\cdot\sin(\psi) \quad \text{[Formula 20]}$$

$$\psi=\arg\{P(x_0-1,y_0,z_0)\cdot P^{\ddagger}(x_0,y_0,z_0)\} \quad \text{[Formula 21]}$$

In the range of [Formula 20], the range of $\psi$ is set from $-\pi/2$ to $\pi/2$, and if $\psi$ is out of the range, a process such as that it is not stored in the list 508 is performed after skipping Step 607. Weighting of [Formula 20] and [Formula 21] becomes small as a phase difference between a pixel of interest and the adjacent pixels is small and becomes small as a difference of signal strength is small. Therefore, in the third method, regional expansion can be performed from a pixel with a small weighting in order while avoiding a region with a large phase change and a large signal strength change.

[Weighting Method 3]

The fourth method sets a product of signal strengths of a pixel of interest and the adjacent pixels or a signal strength of the adjacent pixels as a weighting.

$$W=|P(x_0-1,y_0,z_0)|\cdot|P(x_0,y_0,z_0)| \quad \text{[Formula 22]}$$

$$W=|P(x_0-1,y_0,z_0)| \quad \text{[Formula 23]}$$

By weighting only with a signal strength, regional expansion can be performed while avoiding a region with a low SNR surely.

If a range is set also for a phase difference $\psi$ between a pixel of interest and the adjacent pixel and the phase difference calculated from [Formula 17], [Formula 19], and [Formula 21] is out of the range, limitation can be added to a path for a phase unwrapping process due to regional expansion by performing a process in which the phase difference is not stored in the list 508 after skipping Step 607. There is an advantage that a risk to cause principal value rotation in the phase unwrapping process can be reduced as the range of the phase difference $\psi$ is small, and on the contrary to this, there is a disadvantage that pixels for which regional expansion is not performed are caused.

Although the method 1 in which an inner product of a pixel of interest and the adjacent pixels is set as a weighting is used to determine an order of the regional expansion process in the present embodiment, the other methods may be used.

(Step S607)

Next, according to the weighting calculated in Step 606, the unwrapped phase calculated in Step 605 is stored together with the coordinate in the list 508. The list 508 sets the coordinate and the unwrapped phase for which a weighting was performed as a pair for each pixel and stores it so as to be arranged in the order of weighting.

In case of the inner product weighting that is the method 1 in Step 606, the weighting is stored close to the exit of the list as the value is larger. For example, when the largest weighting is "the weighting 701", the second largest weighting is "the weighting 702", and the third largest weighting is "the weighting 703", the weightings are stored in the order of the weightings 701, 702, and 703 from the one close to the exit of the list of FIG. 7.

In case of the method 2 of Step 606, the weighting is stored close to the exit of the list as the weighting value is larger. In case of the method 3 of Step 606, the weighting is stored close to the exit of the list as the weighting value is smaller. In case of the method 4 of Step 606, the weighting is stored close to the exit of the list as the weighting value is larger. Thus, by storing an unwrapped phase together with the coordinate in the list, phase differences between adjacent pixels and pixels for which an unwrapping process is performed can be reduced to the minimum, which can reduce a memory consumption amount and speed up the processing.

Figure 8:
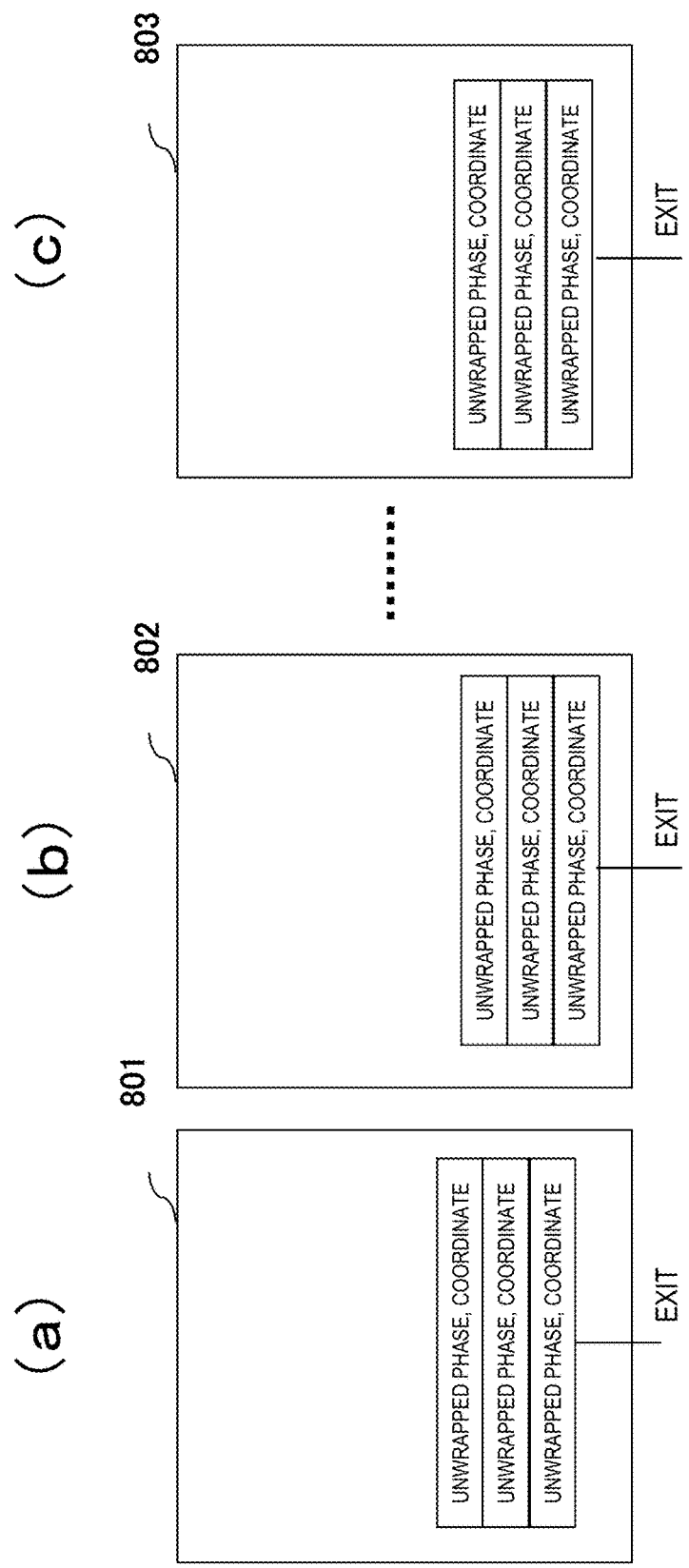
FIG. 8 is an explanatory diagram explaining lists for a high-speed phase unwrapping process: (a) a list of the weighting range 1, (b) a list of the weighting range 2, (c) a list of the weighting range h

In order to speed up the processing more, a plurality of lists should be prepared to select a list in which a weighting is stored according to the weighting value as shown in FIG. 8. This is a method to select a list according to the weighting range so that a weighting value is stored in the list 801 of the weighting range 1 is equal to or less than one-tenth of the maximum signal value, in the list 802 of the weighting range 2 is more than one-tenth of the maximum signal value and equal to or less than two-tenth of the maximum signal value, and in the list 803 of the weighting range h is more than h−1-tenth of the maximum signal value and equal to or less than h-tenth of the maximum signal value in case of setting an inner product as a weighting, i.e. the method 1 of Step 606 after 10 lists are prepared, and the maximum signal value of a phase difference image is calculated in advance, for example. For the lists at this time, the First-in First-out (hereinafter, FIFO) method is used.

That is, a method in which stored data is taken out in order from the oldest and newly stored data is taken out the last is used. Therefore, data is always stored in the farthest position from the exit of each list.

(Step S608)

Figure 7:
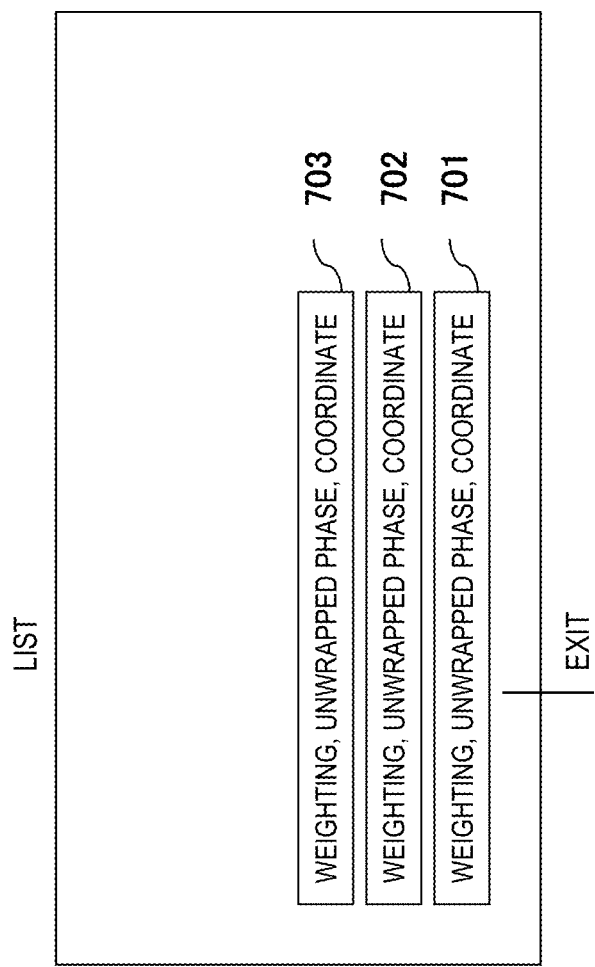
FIG. 7 is an explanatory diagram explaining a list to be used for a phase unwrapping process.

For example, whether a list is empty or not is determined by checking the lists of FIGS. 7 and 8. If there is a list that is not empty, the procedure proceeds to Step 609, and a coordinate and a phase are taken out of the exit of the list. Also, if all the lists are empty, the processing ends. When all the lists become empty, the static magnetic field inhomogeneity map U(x, y, z) 509 is completed. That is, whether all the phase unwrapping processes for pixels that requires a phase unwrapping process due to regional expansion from among the pixels in the phase difference image 506 have ended is checked in Step S608 using the lists of FIGS. 7 and 8, and when all of them are ended, the phase unwrapping process shown in FIG. 6 is ended, and Step S404 of FIG. 4 is executed next. Also, when a phase unwrapping process has not ended, Step S609 is executed to determine a pixel of interest to be processed next using the lists of FIGS. 7 and 8.

(Step S609)

A coordinate and a phase stored in the list 508 are taken out and set as a coordinate and a phase of a pixel of interest. When the list of FIG. 7 is used, the coordinate and the phase are taken out of the exit of the list. Also, when a plurality of lists (FIG. 8) prepared for the speed-up are used, for example, a coordinate and a phase are taken out in order from a list with a large number that is not empty in case of an inner product.

Next, a coordinate and a phase taken out of the list are converted into those of a pixel of interest, and processing is repeated from Step 603. As described above, the phase unwrapping process 403 is performed.

As described above, an unwrapping phase of adjacent pixels for a pixel of interest is calculated in Step S605 of FIG. 6, and weighting for the adjacent pixels is calculated in Step S606. In the present embodiment, adjacent pixels may be pixels directly contacting a pixel of interest, and a few more pixels may be added to the pixels directly contacting the pixel of interest as the adjacent pixels. Additionally, the order of an unwrapping process is described in the above embodiment as if the process were performed for each pixel in order, for example.

However, this was described as a typical example, it is not limited to this. A processing order of two or a few pixels is determined as a unit, and they may be processed in order by adding some width according to the processing order. Even in this way, the present invention can be effective. Particularly in the future, in a case where the number of pixels comprising an image is increased, the above process can be performed also for a plurality of pixels as the unit determining the above order.

Also, a processing width may be changed based on a weighting calculation result. For example, based on the weighting calculation result, it may be configured so that a plurality of pixels are processed all at once in a part where pixels with a large weighting concentrate and so that the number of pixels to be processed all at once is reduced to process them by determining a processing order based on a weighting of each pixel for example in a part where a weighting result is small inversely, that is a part of a low SNR and a part of a large phase difference from a pixel of interest.

Figure 9:
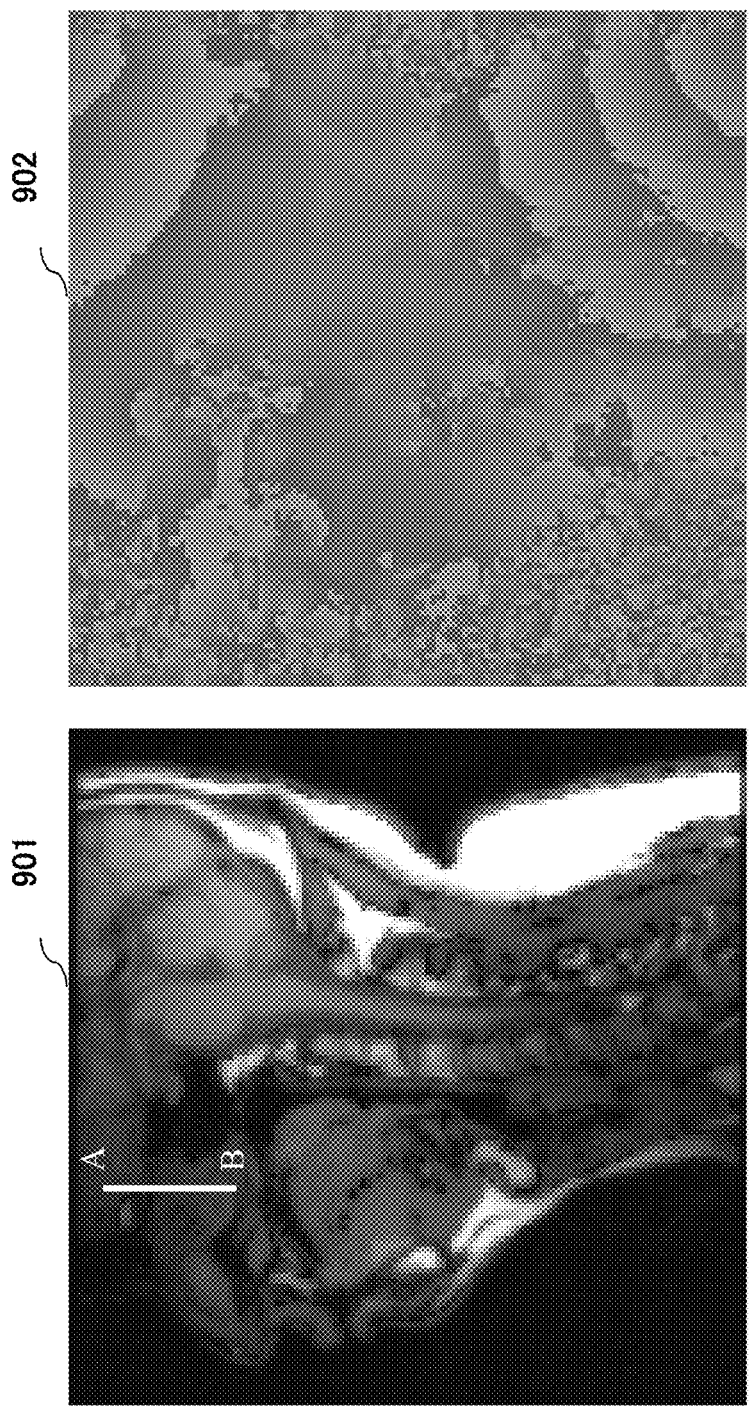
FIG. 9 shows display images explaining phase difference images for simulation of a magnetic resonance imaging apparatus.

Hereinafter, simulation results by the present embodiment are shown. First, the phase difference images described in Step 402 of FIG. 4 are shown in FIG. 9. Additionally, FIG. 9 shows photographs showing the phase difference images. Because phase image data is comprised of complex numbers, they are expressed in an absolute value and a phase. FIG. 9 shows the photographs showing images displaying one slice of the phase difference image 506 in the 2-point Dixon method, and FIG. 901 is a photograph showing an image based on an absolute value of a signal of each pixel in a phase difference image. Also, FIG. 902 is a photograph showing an image based on a signal phase of each pixel in a phase difference image.

Figure 10:
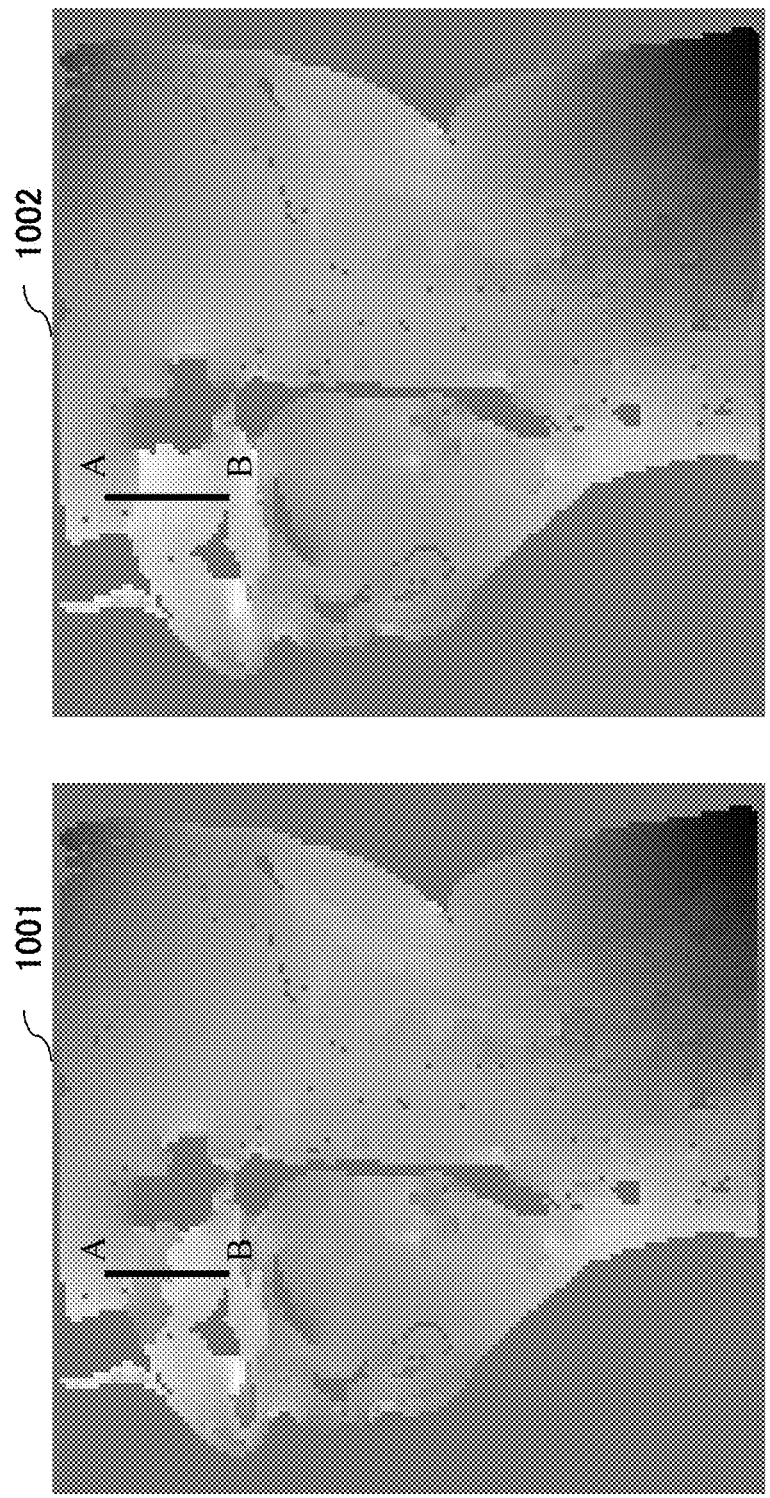
FIG. 10 shows display images explaining a simulated static magnetic field inhomogeneity map of a magnetic resonance imaging apparatus.

Next, phase-unwrapped images described in Step 403 of FIG. 4. FIG. 10 shows photographs showing an image displaying results in which phase unwrapping due to regional expansion was performed for the phase difference images of FIG. 9. FIG. 1001 is a static magnetic field inhomogeneity map generated by performing conventional region expansion (hereinafter, referred to as a conventional method) in a weighting order by a phase difference of adjacent pixels, and FIG. 1002 is a static magnetic field inhomogeneity map generated by performing regional expansion (hereinafter, referred to as the present invention method) in a weighting order by an inner product of adjacent pixels that is an example of the present invention. In FIG. 10, the background region is excluded from regional expansion, simulation is performed using data of 11 slices, and only one slice of them is shown. A difference is found in the result between the point A and the point B in the static magnetic field inhomogeneity map of the conventional method 1001 and the static magnetic field inhomogeneity map of the present invention method 1002 respectively.

Figure 11:
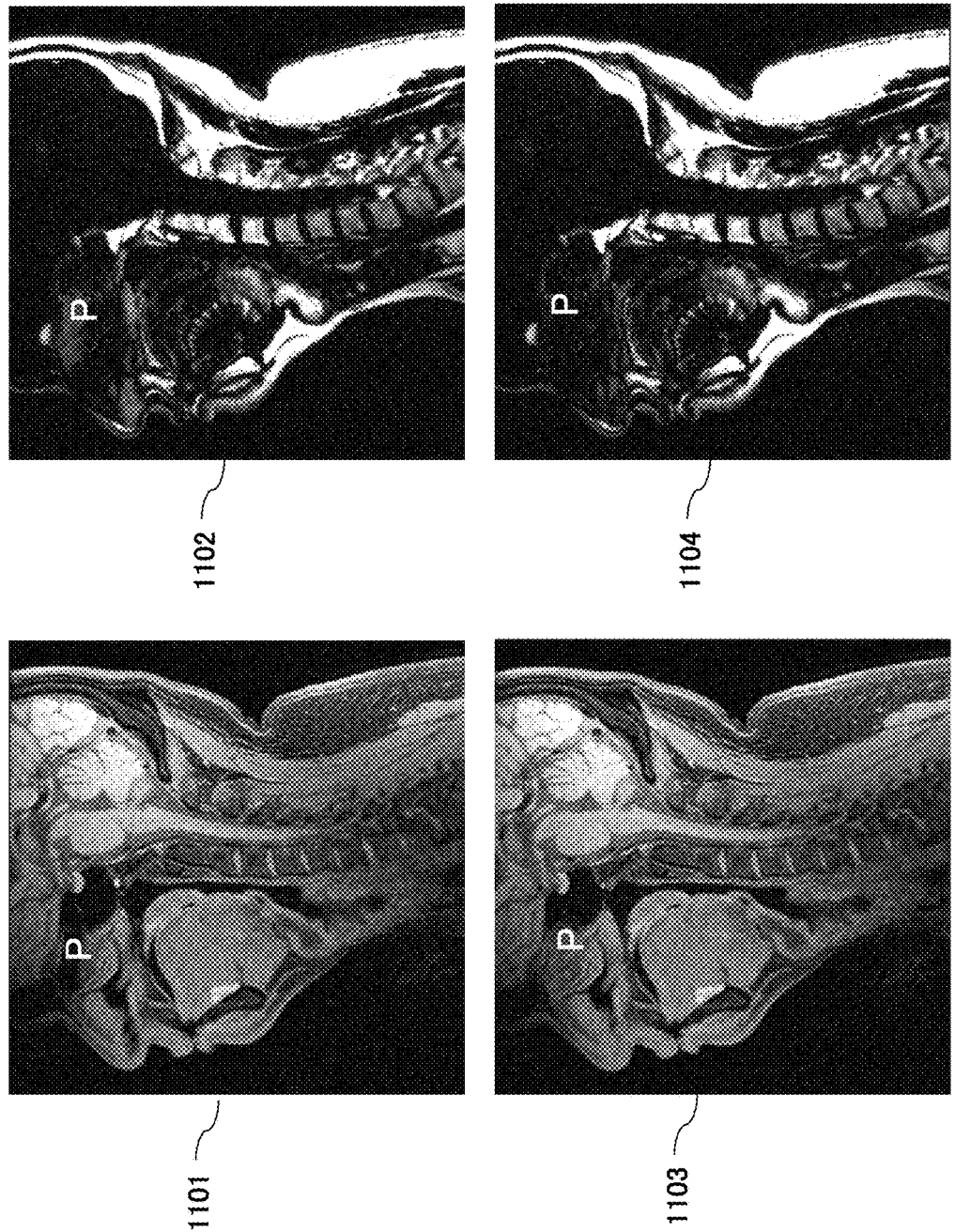
FIG. 11 shows display images showing examples of simulated water and fat images of a magnetic resonance imaging apparatus.

FIG. 11 shows photographs showing images explaining a water image and a fat image of the conventional method as well as a water image and a fat image for which a phase correction process by the 2-point Dixon method described in Step S404 as an example to which the present invention was applied and a water/fat image separation process described in Step S405 were performed. Although water is shown in the fat image at the point P in the water image 1101 and the fat image 1102 of the conventional method, it is found that water and fat are properly separated at the point P in the water image 1103 and the fat image 1104 to which the present invention was applied. This indicates that the static magnetic field inhomogeneity map 1002 to which the present invention was applied is more accurate.

Figure 12:
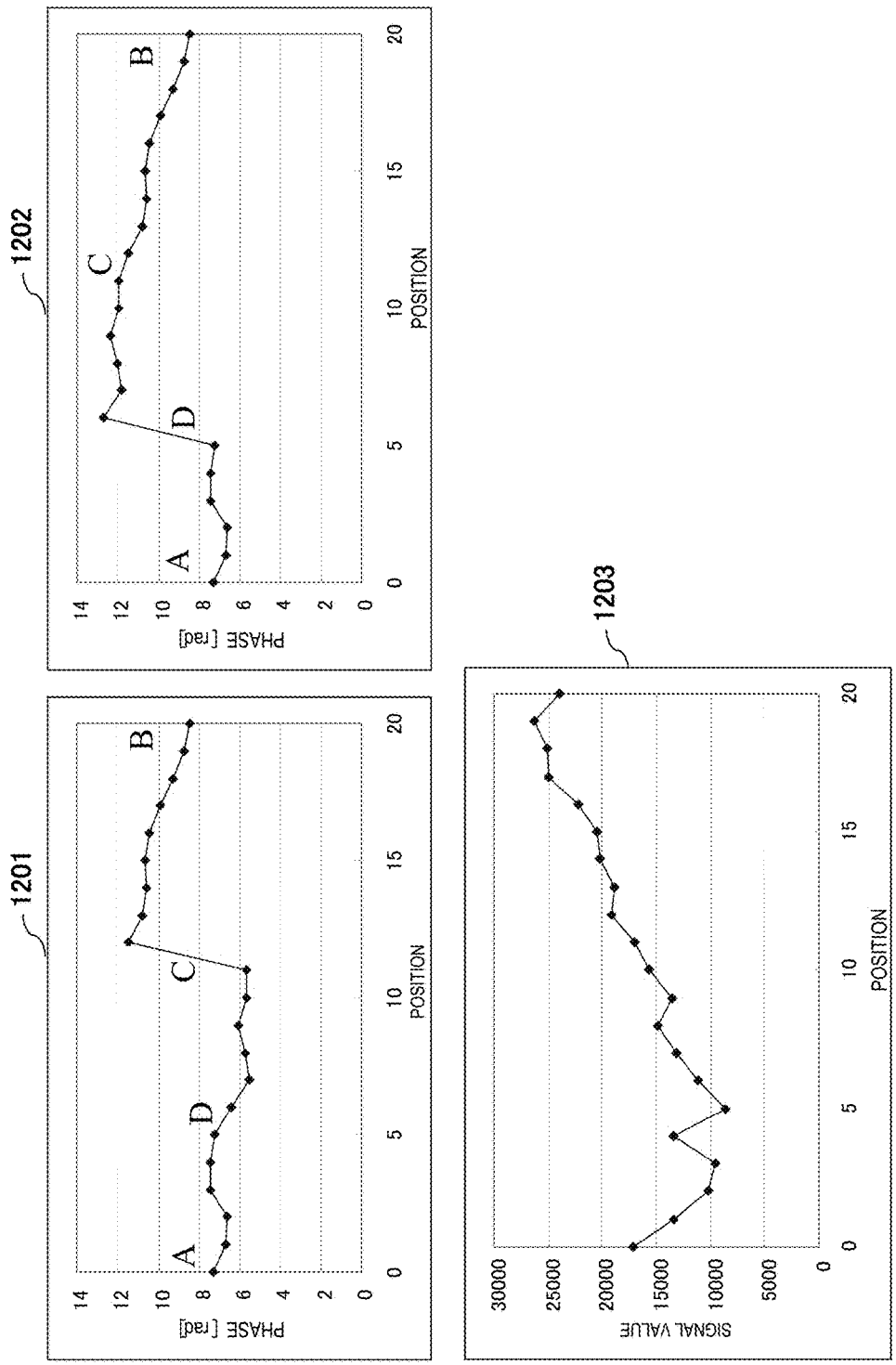
FIG. 12 is explanatory diagrams explaining profiles of the absolute values of simulated static magnetic field inhomogeneity maps and phase difference images.

FIG. 12 is a diagram explaining profiles of absolute values for a static magnetic field inhomogeneity map and a phase difference image. A phase from the point A to the point B in the static magnetic field inhomogeneity map of the conventional method 1001 in FIG. 10 is shown in the profile 1201, and a phase from the point A to the point B in the static magnetic field inhomogeneity map of the present invention method 1002 in FIG. 10 is shown in the profile 1202. Also, signal strengths from the point A to the point B of the absolute value of the phase difference image 901 (FIG. 9) are shown in the profile 1203.

Phase changes at the points C and D are different in profile of the conventional method 1201 and the profile 1202 to which the present invention was applied. The point D is continuous in the profile of the conventional method 1201, a phase at the point C is added by 2π, and principal value rotation occurred at both the points C and D because water in this region was moved to a fat image.

Because phase unwrapping was performed for the point D prior to the point C in phase unwrapping due to regional expansion of the conventional method, principal value rotation occurred at the point D (although a phase had to be added by 2π actually, the point D resulted in being continuous by accident). Then, principal value rotation occurred at the point C without phase unwrapping.

Because phase unwrapping was performed for the point C prior to the point D in phase unwrapping due to regional expansion of the present invention method, a phase was continuous at the point C, a phase was added by 2π at the point D without phase unwrapping, and then principal value rotation did not occur at both the points. This effect was caused by adding signal strength to the priority of regional expansion. Because signal strength at the point D was low in the profile 1203 of an absolute value in a phase difference image, regional expansion could be performed in an application example of the present invention while avoiding the point D where signal strength, i.e. SNR was low, which could obtain the correct static magnetic field inhomogeneity map 1002.

Although the embodiments of the present invention are described above, the present invention can reduce principal value rotation in a phase unwrapping process due to regional expansion and generate a more stable and accurate static magnetic field inhomogeneity map. By generating a accurate static magnetic field inhomogeneity map, a water image a fat image for which the exchange of water and fat was reduced can be obtained.

Also in case of correcting static magnetic field inhomogeneity by automatic shimming (a method to correct static magnetic field inhomogeneity by applying an electric current to a shim coil installed in a gantry), the present invention can be applied when generating a static magnetic field inhomogeneity map.

Because a stable and accurate static magnetic field inhomogeneity map can be generated by applying the present invention, the present invention effectively works on measuring sites for which a static magnetic field inhomogeneity map is subject to inaccuracy, such as cervical vertebrae.

DESCRIPTION OF REFERENCE NUMERALS

1: MRI apparatus, 101: object, 102: static magnetic field magnet, 103: gradient magnetic field coil, 104: irradiation coil, 105: reception coil, 106: bed, 107: gradient magnetic field power source, 108: RF transmission unit, 109: signal detection unit, 110: signal processing unit, 111: display unit, 112: control unit, 201: RF pulse, 202: slice encoding gradient magnetic field, 203: phase encoding gradient magnetic field, 204 and 206: negative-direction frequency encoding gradient magnetic field, 205 and 207: positive-direction frequency encoding gradient magnetic field, 301: signal reception section, 302: k-space database, 303: image conversion section, 304: image database, 305: image processing section, 306: image transmission section, 307: parameter, 501: first echo image, 502: second echo image, 503: mask image generating section, 504: mask image, 505: phase difference image generating section, 506: phase difference image, 507: regional expansion phase unwrapping section, 508: list, 509: static magnetic field inhomogeneity map, 510: phase correcting section, 511: second echo image after phase correction, 512: water/fat image separating section, 701 and 703: weighting, 801 and 803: list, 901: absolute value of the phase difference image, 902: phase of the phase difference image, 1001: static magnetic field inhomogeneity map of the conventional method, 1002: static magnetic field inhomogeneity map of the present invention method, 1101: water image of the conventional method, 1102: fat image of the conventional method, 1103: water image of the present invention method, 1104: fat image of the present invention method, 1201: profile of the conventional method, 1202: profile of the present invention method, 1203: profile of signal strength.

The invention claimed is:

1. A magnetic resonance imaging apparatus comprising:
   a magnetic field generating unit for generating a static magnetic field and a gradient magnetic field to an object;
   a high-frequency pulse irradiating unit for irradiating a high-frequency pulse;
   a reception unit for receiving an NMR signal from the object;
   a display unit for displaying a generated diagnostic image; and
   a signal processing unit for generating a first image based on the NMR signal, determining an order of performing a phase unwrapping process for each pixel forming the first image from among a plurality of pixels for which the phase unwrapping process has not been performed yet and that are adjacent to pixels for which the phase unwrapping process has already been performed within the pixels of the first image by selecting unprocessed pixels with a high signal strength preferentially, and generating a second image by performing a phase unwrapping process for the unprocessed pixels in the determined order.

2. The magnetic resonance imaging apparatus according to claim 1,
   wherein the signal processing unit determines the order of performing the phase unwrapping process by preferentially selecting unprocessed pixels with a small phase difference for signals of the processed pixels in addition to the high signal strength.

3. The magnetic resonance imaging apparatus according to claim 1,
wherein the first image is a phase difference image, and the second image is a correction map,
the signal processing unit performs a phase unwrapping process for a signal of the phase difference image for each pixel in the said order to generate the correction map,
the signal processing unit determines the said order of performing the phase unwrapping process for the unprocessed pixels of the phase difference image by preferentially selecting the unprocessed pixels with a high signal strength and a small phase difference for signals of the processed pixels from among a plurality of the unprocessed pixels adjacent to the processed pixels in the phase difference image and further generates a water image or a fat image, based on the correction map, and
the display unit displays at least either one of the water image or the fat image.

4. The magnetic resonance imaging apparatus according to claim 3,
wherein the signal processing unit generates at least first and second images based on the NMR signal from the reception unit, further generates the phase difference image having a complex signal expressed in a complex number for each pixel based on the first and second images, performs weighting by calculating the complex signal of the unprocessed pixels in the phase difference image, and determines the said order of performing a phase unwrapping process for the unprocessed pixels based on the weighting.

5. The magnetic resonance imaging apparatus according to claim 4,
wherein the signal processing unit calculates the weighting based on calculation for a product of complex signals of the processed pixels and complex signals of the unprocessed pixels.

6. The magnetic resonance imaging apparatus according to claim 4,
wherein the signal processing unit calculates the weighting by calculating differences between the complex signals of the processed pixels and the complex signals of the unprocessed pixels.

7. The magnetic resonance imaging apparatus according to claim 3,
wherein the signal processing unit generates at least a first echo image and a second echo image based on the NMR signal from the reception unit,
the signal processing unit generates a mask image based on the first echo image or the second echo image,
the signal processing unit generates the phase difference image based on the first echo image or the second echo image, and
the signal processing unit performs a phase unwrapping process for pixels that are not masked in the mask image from among the pixels in the phase difference image for each of the pixels in the said order to generate a static magnetic field inhomogeneity map.

8. The magnetic resonance imaging apparatus according to claim 3,
wherein the signal processing unit generates at least a first echo image and a second echo image based on the NMR signal from the reception unit, further generates the phase difference image based on the first echo image and the second echo image, generates a static magnetic field inhomogeneity map by performing a phase unwrapping process for the unprocessed pixels in the phase difference image in the said order, and generates at least either one of a water image and a fat image based on the static magnetic field inhomogeneity map, and
the display unit displays at least either one of the water image and the fat image as the diagnostic image.

9. The magnetic resonance imaging apparatus according to claim 8,
wherein after the high-frequency pulse is irradiated from the high-frequency pulse irradiating unit, a first NMR signal is received after a first time where the NMR signals from water and fat become opposite phases each other elapses; or after the high-frequency pulse is irradiated, a second NMR signal is received after a second time where the NMR signals from water and fat become the same phase each other elapses, and then the first echo image is generated by the first NMR signal; the second echo image is generated by the second NMR signal, and
a phase unwrapping process is performed for the phase difference image to generate a static magnetic field inhomogeneity map, and then at least the water image or the fat image is generated based on the static magnetic field inhomogeneity map, the first echo image, and the second echo image.

10. The magnetic resonance imaging apparatus according to claim 9,
wherein the high-frequency pulse is irradiated from the high-frequency pulse irradiating unit in a state where a gradient magnetic field is generated by the magnetic field generating unit, and then the magnetic field generating unit further generates a gradient magnetic field and also generates a negative-direction encoding gradient magnetic field,
an encoding gradient magnetic field of a first polarity is generated to receive the first NMR signal at a time point when the first time elapses from the high-frequency pulse irradiation,
and/or
an encoding gradient magnetic field of a second polarity is generated to receive the second NMR signal at a time point when the second time elapses from the high-frequency pulse irradiation,
the encoding gradient magnetic field is changed to repeatedly receive the first NMR signal and the second NMR signal, and
the signal processing unit performs image conversion for the received first NMR signal and second NMR signal respectively to generate the first echo image and the second echo image.

11. The magnetic resonance imaging apparatus according to claim 3,
wherein the signal processing unit sets the processed pixel for which a phase unwrapping process was performed last from among the processed pixels as a pixel of interest, performs a weighting calculation for the unprocessed pixels adjacent to the pixel of interest based on a signal strength of the unprocessed pixels and a phase difference between signals of the unprocessed pixels for a signal of the pixel of interest, creates a list in which data about each of the unprocessed pixels is arranged in order according to the result of the weighting calculation for each of the unprocessed pixels, determines a new pixel of interest according to the list to set the unwrapping phase as a phase of a corresponding pixel of a static magnetic field inhomogeneity map, and repeats the above process again for the new pixel of interest.

12. The magnetic resonance imaging apparatus according to claim 2,
wherein the signal processing unit calculates an inner product of a signal of the processed pixel and each signal of the multiple unprocessed pixels adjacent to the processed pixel and determines unprocessed pixels for which a phase unwrapping process should be performed from among the unprocessed pixels according to the result of calculation for the inner product.

13. The magnetic resonance imaging apparatus according to claim 2,
wherein the phase unwrapping process performed by the signal processing unit is to set a phase in which the unwrapping process was performed for each pixel comprising a phase difference image that is the first image as a phase of corresponding pixels of the second image,
after the high-frequency pulse is irradiated from the high-frequency pulse irradiating unit, a first NMR signal is received at a time point when a first time where the NMR signals from water and fat become opposite phases each other elapses; or after the high-frequency pulse is irradiated, a second NMR signal is received at a time point when a second time where the NMR signals from water and fat become the same phase each other elapses,
the signal processing unit performs image conversion based on the first NMR signal to generate a first echo image or performs image conversion based on the second NMR signal to generate a second echo image,
the signal processing unit generates the phase difference image that is the first image based on the first echo image and the second echo image, further determines a pixel of interest to start the said process from among the unprocessed pixels of pixels comprising the phase difference image, and sets a phase in which an unwrapping process was performed for the pixel of interest as a phase of corresponding pixels of the second image,
the signal processing unit further determines whether there are unprocessed pixels adjacent to the pixel of interest or not and stores a priority to the unprocessed pixels and a phase for which an unwrapping process was performed as a list in which each of the unprocessed pixels is a unit if there are unprocessed pixels, the signal processing unit selects unprocessed pixels to be processed according to the priority based on the stored list, sets the phase for which an unwrapping process was performed of the selected unprocessed pixels as a phase of corresponding pixels of the second image, and further repeats the said operation by setting the selected unprocessed pixels as a new pixel of interest, and
the signal processing unit sets a phase for which an unwrapping process was performed for each pixel comprising the phase difference image according to the said priority for corresponding pixels of the second image respectively to generate the second image.

14. A processing method of a magnetic resonance imaging apparatus, comprising: a magnetic field generating unit for generating a static magnetic field and a gradient magnetic field to an object; a high-frequency pulse irradiating unit for irradiating a high-frequency pulse; a reception unit for receiving an NMR signal from the object; a signal processing unit for performing signal processing; and a display unit for displaying a diagnostic image,
wherein the signal processing unit generates a first image based on the NMR signal,
the signal processing unit performs weighting based on a signal strength and a phase difference for signals of the processed pixels from among a plurality of unprocessed pixels for which an phase unwrapping process has not been performed yet that are adjacent to processed pixels for which the phase unwrapping process has been already performed of the first image,
the signal processing unit selects pixels for which a phase unwrapping process is performed next from among the unprocessed pixels based on the weighting and generates a second image by processing the unprocessed pixels in order, and
the signal processing unit further constructs the diagnostic image using the second image.

15. The processing method of a magnetic resonance imaging apparatus according to claim 14,
wherein the signal processing unit calculates an inner product of a signal of the processed pixel of the first image and each signal of the multiple unprocessed pixels adjacent to the processed pixel, performs the weighting according to the result of the calculated inner product, and selects unprocessed pixels for which a phase unwrapping process should be performed next from among the unprocessed pixels according to the weighting.

* * * * *